United States Patent
Jinno

(10) Patent No.: US 7,315,379 B2
(45) Date of Patent: Jan. 1, 2008

(54) EVALUATING METHOD AND APPARATUS THEREOF

(75) Inventor: Takayuki Jinno, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/742,065

(22) Filed: Apr. 30, 2007

(65) Prior Publication Data

US 2007/0201029 A1 Aug. 30, 2007

Related U.S. Application Data

(63) Continuation of application No. PCT/JP2006/305259, filed on Mar. 16, 2006.

(30) Foreign Application Priority Data

Mar. 22, 2005 (JP) .............................. 2005-082709

(51) Int. Cl.
*G01N 21/55* (2006.01)
*G01N 21/47* (2006.01)
*G01B 11/30* (2006.01)

(52) U.S. Cl. ...................... 356/445; 356/446; 356/600

(58) Field of Classification Search ................ 356/369, 356/600, 445–446; 399/38; 250/559.01–559.19
See application file for complete search history.

(56) References Cited

U.S. PATENT DOCUMENTS

| | | | | |
|---|---|---|---|---|
| 3,850,526 A | * | 11/1974 | Corey, III | 356/512 |
| 3,922,093 A | * | 11/1975 | Dandliker et al. | 356/600 |
| 4,139,307 A | * | 2/1979 | Clarke | 356/446 |
| 4,606,645 A | * | 8/1986 | Matthews et al. | 356/446 |
| 4,613,235 A | * | 9/1986 | Suga | 345/446 |
| 4,746,805 A | * | 5/1988 | Stapleton | 250/559.16 |
| 4,750,140 A | * | 6/1988 | Asano et al. | 382/108 |
| 4,830,504 A | * | 5/1989 | Frohardt et al. | 356/448 |
| 4,886,355 A | * | 12/1989 | Keane | 356/73 |
| 4,945,253 A | * | 7/1990 | Frohardt | 250/559.16 |
| 5,155,558 A | * | 10/1992 | Tannenbaum et al. | 356/446 |
| 5,252,836 A | * | 10/1993 | Matthews et al. | 250/559.18 |
| 5,401,977 A | * | 3/1995 | Schwarz | 250/559.1 |
| 5,416,594 A | * | 5/1995 | Gross et al. | 356/237.5 |
| 6,560,351 B1 | * | 5/2003 | Hirota | 382/108 |

FOREIGN PATENT DOCUMENTS

| | | |
|---|---|---|
| EP | 0 183 270 | 6/1986 |
| JP | 62-126331 | 6/1987 |
| JP | 4-315952 | 11/1992 |
| JP | 6-242016 | 9/1994 |
| JP | 2004-286672 | 10/2004 |
| JP | 2004-317131 | 11/2004 |

\* cited by examiner

*Primary Examiner*—Gregory J. Toatley, Jr.
*Assistant Examiner*—Jarreas Underwood
(74) *Attorney, Agent, or Firm*—Fitzpatrick, Cella, Harper & Scinto

(57) ABSTRACT

A measurement apparatus measures the spatial distributed characteristic of reflection of an object. Evaluate parameters used to evaluate the gloss character of the object are extracted based on the measurement result. An evaluate value indicating the gloss character of the object is calculated based on the extracted evaluate parameters. The calculated evaluate value is visually displayed on at least a two-dimensional space specified by the evaluate parameters.

16 Claims, 13 Drawing Sheets

EVALUATING METHOD AND APPARATUS THEREOF

This application is a continuation of International Application No. PCT/JP2006/305259 filed Mar. 16, 2006.

TECHNICAL FIELD

The present invention relates to an evaluating method and apparatus for calculating evaluation values associated with gloss and gloss nonuniformity of an object. For example, the present invention relates to an evaluating method and apparatus thereof for calculating an evaluation value with a high correlation with subjective gloss of an image observer in association with a printing medium such as a hard copy or the like printed by an image output apparatus such as a color printer or the like.

BACKGROUND ART

The gloss of a printing medium printed by an image output apparatus such as a color printer or the like is an important image quality factor in the field of photo printing and document printing, and is used as one of quality management items of printing media. The printing media have different gloss states of their surfaces depending on print methods, color materials, paper sheets, and the like.

An evaluation method of the gloss of a printing medium generally uses a measured value of a glossiness meter compliant with a specular glossiness measurement method (JIS Z 8741) that measures the intensity of specular reflected light. Glossiness evaluation of a highly gloss object such as the outer panels of an automobile uses a measured value of haze meter compliant with reflection hase measurement method (ISO 13803, ASTM E 430) for measuring the tarnish degree of a sample surface, and an image clarity measurement method (JIS K 7105, JIS H 8686) for measuring the distinctness of image that appears on a sample surface.

While printing with electro-photographic printer uses pigment toner and pigment ink inkjet printers, color materials remain on the surface of media other than infiltrating the printing medium. Therefore, the surface structure and color material, which have different refractive index from media, exposure ratio of printings vary according to colors and densities that cause gloss nonuniformity.

As a method of evaluating the gloss of an object in such an environment, for example, patent reference 1 is known. This patent reference 1 uses, as a gloss evaluation value, a linear sum of a gloss index value obtained based on specular reflected light and an index value associated with lightness obtained based on diffused reflected light.

Patent reference 1: Japanese Patent Laid-Open No. 2004-317131

DISCLOSURE OF INVENTION

Problems that the Invention is to Solve

However, the measured value of the glossiness meter based on the specular glossiness measurement method, a haze meter based on the reflection haze measurement method, and an image clarity measurement apparatus based on the image clarity measurement method do not often correspond to human visual evaluation.

The specular glossiness measurement method measures only the intensity of specular light. However, observer evaluates gloss based on not only on the intensity of specular reflected light but also on a spatial distributed characteristic of reflection in the neighborhood of specular reflection. For this reason, if printing samples to be evaluated include samples having a broad reflected light distribution in the neighborhood of specular reflection and those having a narrow reflected light distribution, the result is a poor correlation between an objective evaluate value and subjective evaluate values measured by the specular glossiness measurement method.

By contrast, the reflection haze measurement method and image clarity measurement method do not measure the intensity of specular reflected light, but they measure only the reflected light intensity in the neighborhood of specular reflection or components corresponding to a spread in the neighborhood of specular reflection. For this reason, these methods cannot detect a gloss difference due to the intensity difference of specular reflected light, and the result is a poor correlation between an objective evaluate value and subjective evaluate values measured by the specular glossiness measurement method.

That is, the generally used measurement methods cannot measure physical elements enough to evaluate gloss.

Furthermore, evaluation of gloss nonuniformity uses only an objective evaluate value measured by the specular glossiness measurement method or that which is measured by the reflection haze measurement method and image clarity measurement method. For this reason, for the same reason as the reason for non-correspondence between the conventional gloss evaluation value and human visual evaluation, these objective evaluation values do not correspond to the human visual evaluation.

The present invention has been made to solve the aforementioned problems, and has as its object to provide an evaluation method and apparatus which can calculate a gloss evaluate value gloss nonuniformity evaluation value having high correlation with subjective evaluation of gloss.

Means of Solving the Problems

In order to achieve the above object, an evaluating method according to the present invention comprises the following configuration.

That is, an evaluating method of evaluating a gloss character of an object using an image processing apparatus, comprises:

a measurement step of measuring a spatial distributed characteristic of reflection of the object using a goniometric measurement apparatus;

an extraction step of extracting evaluate parameters used to evaluate the gloss character of the object based on a measurement result in the measurement step;

a calculation step of calculating an evaluate value indicating the gloss character of the object based on the evaluate parameters extracted in the extraction step; and a display step of visually displaying the evaluate value calculated in the calculation step on at least a two-dimensional space specified by the evaluate parameters.

Preferably, the spatial distributed characteristic of reflection is a distribution character of a reflected light intensity from the object in the neighborhood of specular reflection.

Preferably, the measurement apparatus comprises:

a light source for illuminating an object to be evaluated with light; and a light-receiving device for making a goniometric measurement of a spatial distribution of reflected light at a to-be-measured part illuminated with light from the illumination means from an identical circumference.

Preferably, the evaluate parameters include a specular reflected light intensity and a specular reflection neighboring light intensity.

Preferably, the evaluate parameters include a specular reflected light intensity and a spread of a reflected light distribution in the neighborhood of specular reflection.

Preferably, the evaluate parameters include a specular glossiness value measured based on a specular glossiness measurement method, and a reflection haze value measured based on a reflection haze measurement method.

Preferably, the evaluate parameters include a specular glossiness value measured based on a specular glossiness measurement method, and an image clarity value measured based on an image clarity measurement method.

Preferably, the gloss character is gloss of the object, and the calculation step includes a step of calculating an evaluate value associated with the gloss of the object.

Preferably, the gloss character is gloss nonuniformity between a plurality of objects, and the calculation step includes a step of calculating an evaluate value associated with the gloss nonuniformity between the plurality of objects.

Preferably, the calculation step includes a step of calculating the evaluate value associated with the gloss by calculating based on an intensity of specular reflected light and an intensity of reflected light in the neighborhood of specular reflection, which are obtained from the spatial distributed characteristic of reflection:

$$G_V = \alpha G_Y + \beta G_X + \gamma$$

$$\begin{pmatrix} G_V: \text{glossiness evaluation value} \\ G_Y: \text{regular reflected light intensity} \\ G_X: \text{regular reflection neighboring reflected light intensity} \\ \alpha, \beta: \text{weighting coefficients} \\ \gamma: \text{constant} \end{pmatrix}$$

Preferably, the calculation step includes a step of calculating the evaluate value associated with the gloss nonuniformity between the plurality of objects by calculating based on intensities of specular reflected light and intensities of reflected light in the neighborhood of specular reflection on the plurality of objects, which are obtained from thea spatial distributed characteristic of reflection:

$$\sigma(G_X, G_Y) = \sqrt{\frac{n\sum G_Y^2 - (\sum G_Y)^2}{n(n-1)}} \cdot \sqrt{\frac{n\sum G_X^2 - (\sum G_X)^2}{n(n-1)}}$$

$$\begin{pmatrix} G_Y: \text{regular reflected light intensity} \\ G_X: \text{regular reflection neighboring reflected light intensity} \\ \sigma(G_Y, G_X): \text{gloss nonuniformity evaluation value} \\ n: \text{number of objects to be evaluated} \end{pmatrix}$$

Preferably, the calculation step includes a step of calculating nonuniformity components of intensities of specular reflected light and nonuniformity components of reflected light in the neighborhood of specular reflection between the plurality of objects by calculating based on the intensities of specular reflected light and the intensities of reflected light in the neighborhood of specular reflection on the plurality of objects, which are obtained from thea spatial distributed characteristic of reflection:

$$\sigma(G_Y) = \sqrt{\frac{n\sum G_Y^2 - (\sum G_Y)^2}{n(n-1)}}$$

$$\sigma(G_X) = \sqrt{\frac{n\sum G_X^2 - (\sum G_X)^2}{n(n-1)}}$$

$$\begin{pmatrix} G_Y: \text{regular reflected light intensity} \\ G_X: \text{regular reflection neighboring reflected light intensity} \\ \sigma(G_Y): \text{nonuniformity component in regular reflected light intensity} \\ \sigma(G_X): \text{nonuniformity component in regular reflection} \\ \quad \text{neighboring light intensity} \\ n: \text{number of objects to be evaluated} \end{pmatrix}$$

In order to achieve the above object, an evaluating apparatus according to the present invention comprises the following arrangement.

That is, an evaluating apparatus for evaluating a gloss character of an object, comprises:

measurement means for measuring a spatial distributed characteristic of reflection of the object;

extraction means for extracting evaluate parameters used to evaluate the gloss character of the object based on a measurement result of the measurement means;

calculation means for calculating an evaluate value indicating the gloss character of the object based on the evaluate parameters extracted by the extraction means; and display means for visually displaying the evaluate value calculated by the calculation means on at least a two-dimensional space specified by the evaluate parameters.

EFFECTS OF THE INVENTION

According to the present invention, an evaluating method and apparatus which can calculate a gloss evaluate value and gloss nonuniformity evaluate value which have high correlation with subjective gloss are provided.

Other features and advantages of the present invention will be apparent from the following description taken in conjunction with the accompanying drawings, in which like reference characters designate the same or similar parts throughout the figures thereof.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF REFERENCE NUMERALS

Figure 1:
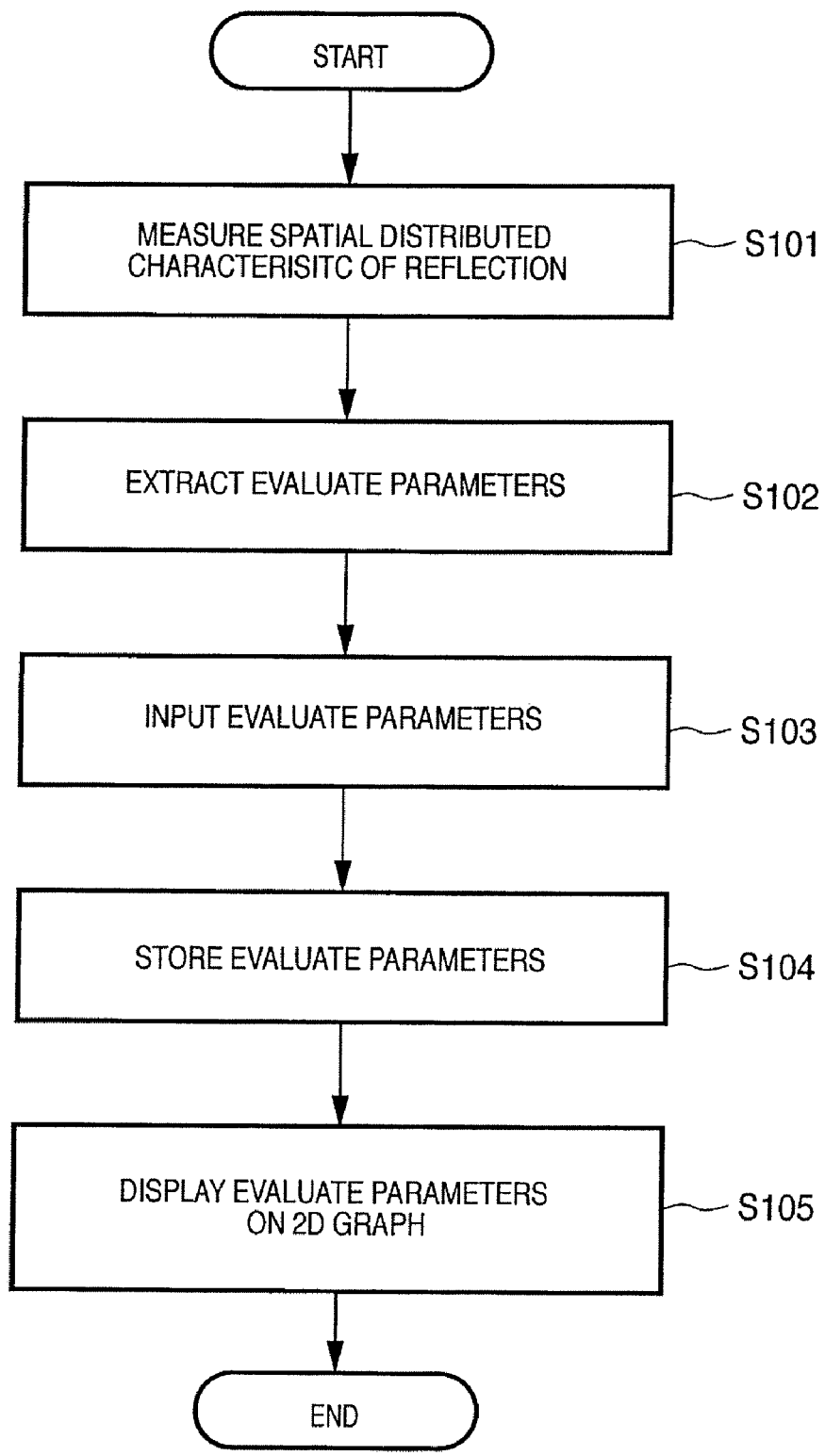
FIG. 1 is a flowchart showing an overview of gloss evaluating processing according to the first embodiment of the present invention.

100 Gloss evaluating apparatus
210 Received light signal processor
211 Photometry unit
213 Evaluate parameter extraction unit
214 Specular reflected light intensity extraction unit
215 Specular reflection neighboring light intensity extraction unit
220 Gloss evaluate value calculation processor
221 Evaluate parameter input unit
222 Specular reflected light intensity input unit
223 Specular reflection neighboring light intensity input unit
224 Evaluate parameter storage unit
230 Gloss evaluate value output unit
231 Gloss evaluate value file output unit
232 Gloss evaluate value monitor display unit Best Mode for Carrying Out the Invention Embodiments of the present invention will be described in detail hereinafter with reference to the accompanying drawings.

First Embodiment

An overview of gloss evaluating processing by a gloss evaluating apparatus (image processing apparatus) according to the first embodiment will be described first using FIG. 1.

FIG. 1 is a flowchart showing an overview of the gloss evaluating processing according to the first embodiment of the present invention.

Note that FIG. 1 shows processing until a gloss evaluate value of a printing medium to be evaluated is output onto a two-dimensional graph used to evaluate gloss.

Assume that a printing medium as an object which is to undergo gloss (gloss character) evaluation includes not only paper used in a normal printing apparatus but also media in a broad range such cloth, a plastic film, a metal plate, and the like, which can accept printing agents used in the printing apparatus.

Referring to FIG. 1, the spatial distributed characteristic of reflection of a printing medium to be evaluated is measured (step S101) Evaluate parameters are extracted from the spatial distributed characteristic of reflection measured in step S101 (step S102). The evaluate parameters extracted in step S102 are input (step S103). The evaluate parameters input in step S103 are stored (step S104). The evaluate parameters input in step S104 are displayed on a two-dimensional graph (step S105).

The contents of the processes in respective steps in FIG. 1 will be described in detail below with reference to FIGS. 2A to 9.

Figure 2A:
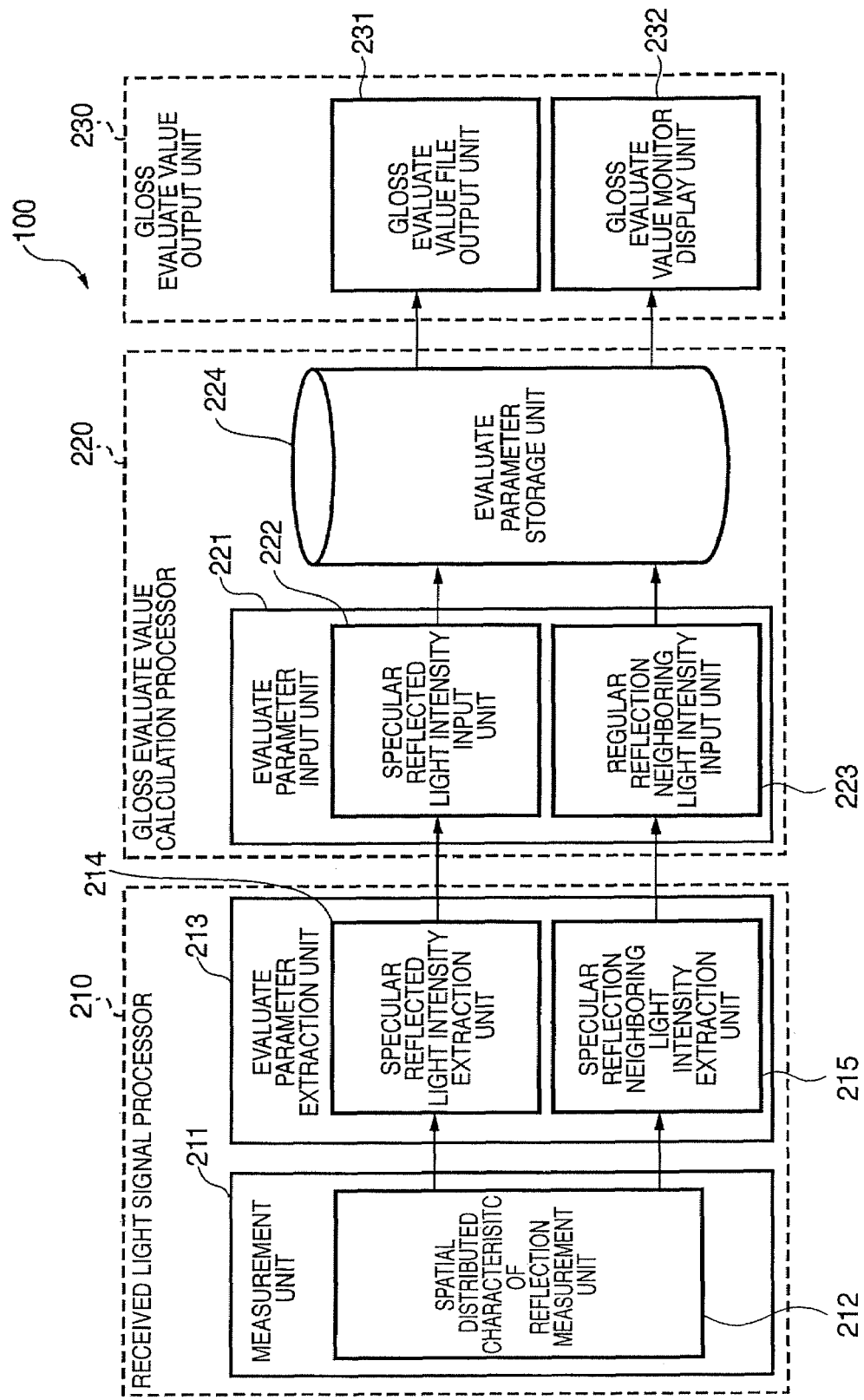
FIG. 2A is a schematic block diagram showing the overall arrangement of a gloss evaluating apparatus according to the first embodiment of the present invention.

FIG. 2A is a schematic block diagram showing the overall arrangement of a gloss evaluating apparatus according to the first embodiment of the present invention.

A gloss evaluating apparatus 100 comprises a received light signal processor 210, gloss evaluate value calculation processor 220, and gloss evaluate value output unit 230.

The received light signal processor 210 includes a photometry unit 211 and evaluate parameter extraction unit 213. The photometry unit 211 executes the process in step S101, and a spatial distributed characteristic of reflection measurement unit 212 in the photometry unit 211 measures the spatial distributed characteristic of reflection of the surface of the printing medium to be evaluated. The evaluate parameter extraction unit 213 executes the process in step S102, and a specular reflected light intensity extraction unit 214 and specular reflection neighboring light intensity extraction unit 215 respectively extract a specular reflected light intensity and specular reflection neighboring light intensity from the spatial distributed characteristic of reflection of the printing medium surface measured by the spatial distributed characteristic of reflection measurement unit 212.

The gloss evaluate value calculation processor 220 includes an evaluate parameter input unit 221 and evaluate parameter storage unit 224. The evaluate parameter input unit 221 executes the processing in step S103, and a specular reflected light intensity input unit 222 inputs the specular reflected light intensity extracted by the specular reflected light intensity extraction unit 214. Also, a specular reflection neighboring light intensity input unit 223 inputs the specular reflection neighboring light intensity extracted by the specular reflection neighboring light intensity extraction unit 215. The evaluate parameter storage unit 224 executes the process in step S104, and a storage medium such as a memory of a computer or the like stores the specular reflected light intensity and specular reflection neighboring light intensity input by the evaluate parameter input unit 221.

The gloss evaluate value output unit 230 includes a gloss evaluate value file output unit 231 and gloss evaluate value monitor display unit 232. The gloss evaluate value output unit 230 executes the process in step S105, and the gloss evaluate value file output unit 231 outputs a pair of the specular reflected light intensity and specular reflection neighboring light intensity stored by the evaluate parameter storage unit 224 to a file in a predetermined format. The gloss evaluate value monitor display unit 232 displays the pair of the specular reflected light intensity and specular reflection neighboring light intensity stored by the evaluate parameter storage unit 224 or an optical character (gloss evaluate value) obtained based on that pair on a two-dimensional (2D) graph on the monitor of a terminal such as a computer or the like.

The hardware arrangement that implements the gloss evaluating apparatus will be described below using FIG. 2B.

Figure 2B:
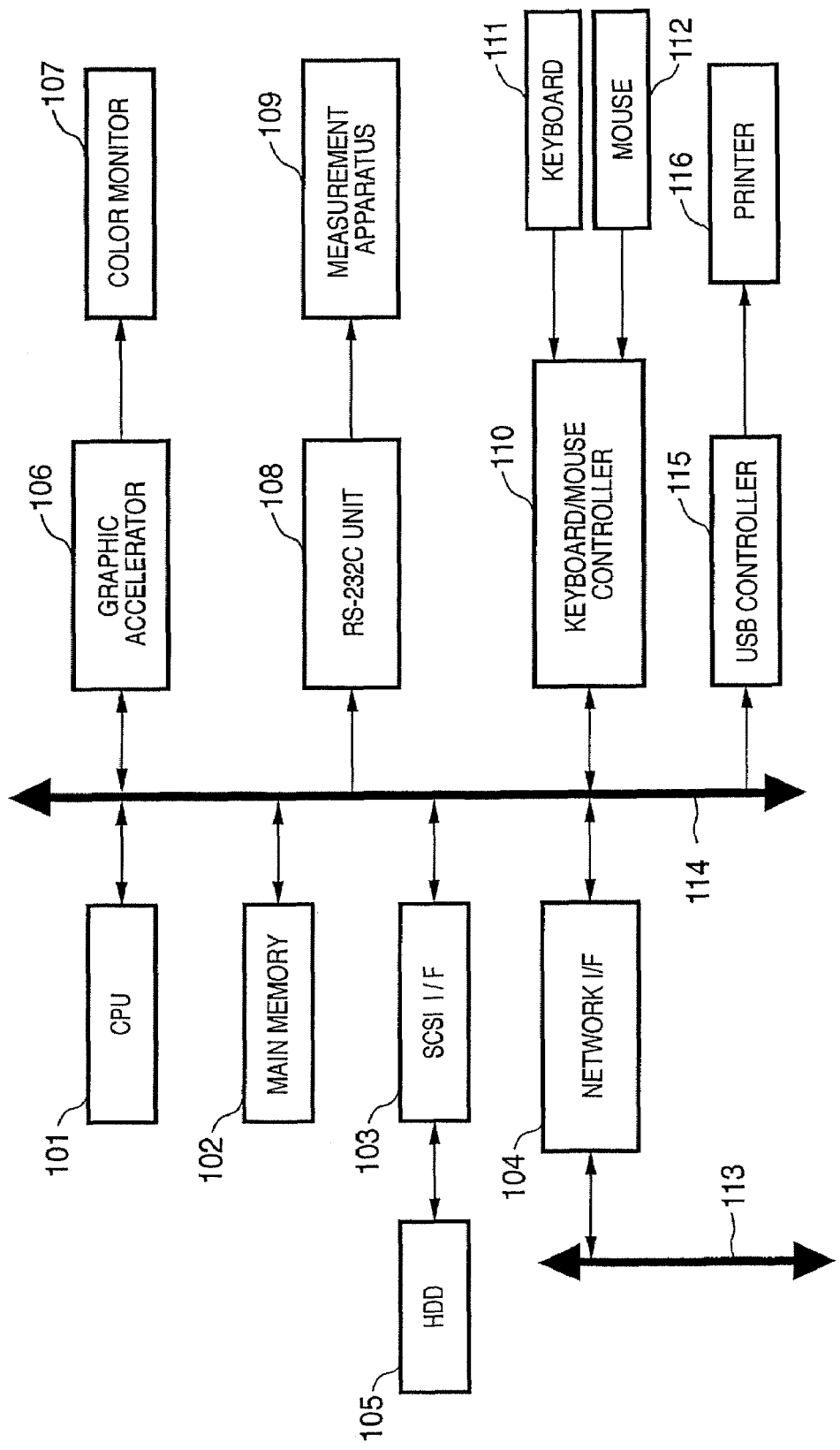
FIG. 2B is a block diagram showing the hardware arrangement of the gloss evaluating apparatus according to the first embodiment of the present invention.

FIG. 2B is a block diagram showing the hardware arrangement of the gloss evaluating apparatus according to the first embodiment of the present invention.

Referring to FIG. 2B, reference numeral 101 denotes a CPU, which controls respective building components which form the gloss evaluating apparatus. Reference numeral 102 denotes a main memory, which comprises a RAM, ROM, and the like, and the RAM serves as a data work area and temporary save area. The ROM stores various control programs including programs which implement respective embodiments of the present invention.

Reference numeral 103 denotes a SCSI interface (I/F), which connects a SCSI device (e.g., an HDD 105) and controls data transfer to it. Reference numeral 104 denotes a network interface (I/F) which connects an external network (local area network 113) and controls data exchange via that network. Reference numeral 105 denotes an HDD (hard disk drive), which stores various control programs (an OS and various applications) and various data such as setting data and the like.

Note that this embodiment has exemplified a SCSI HDD as the HDD. However, the present invention is not limited to this, and HDDs of other types, e.g., an IDE HDD, SATA HDD, and the like may be used. In this case, interfaces according to the HDD types are used, needless to say.

Reference numeral 106 denotes a graphic accelerator, which controls display of images (e.g., various interfaces generated under the control of the CPU 101) to be output to a color monitor 107. Reference numeral 107 denotes a color monitor which comprises, e.g., a liquid crystal projector.

Reference numeral 108 denotes an RS-232C unit, which connects a measurement apparatus 109 and controls that apparatus. Reference numeral 109 denotes a measurement apparatus which measures spatial distributed reflection of an object to be processed. Reference numeral 110 denotes a keyboard/mouse controller, which connects input devices (keyboard 111 and mouse 112) and controls these devices. Reference numeral 111 denotes a keyboard; and 112, a mouse. Reference numeral 113 denotes a local area network.

Reference numeral 115 denotes a USB controller, which connects a USB device (e.g., a color printer 1116) and controls that device. Reference numeral 116 denotes a color printer, which includes various printing schemes such as an ink-jet scheme, laser beam scheme, and the like. Reference numeral 114 denotes a system bus, which comprises a PCI bus, ISA bus, or the like, and interconnects the respective building components which form the gloss evaluating apparatus.

The overall arrangement and operation of the measurement apparatus which implements the spatial distributed characteristic of reflection measurement unit 212 will be described below using FIG. 3.

Figure 3:
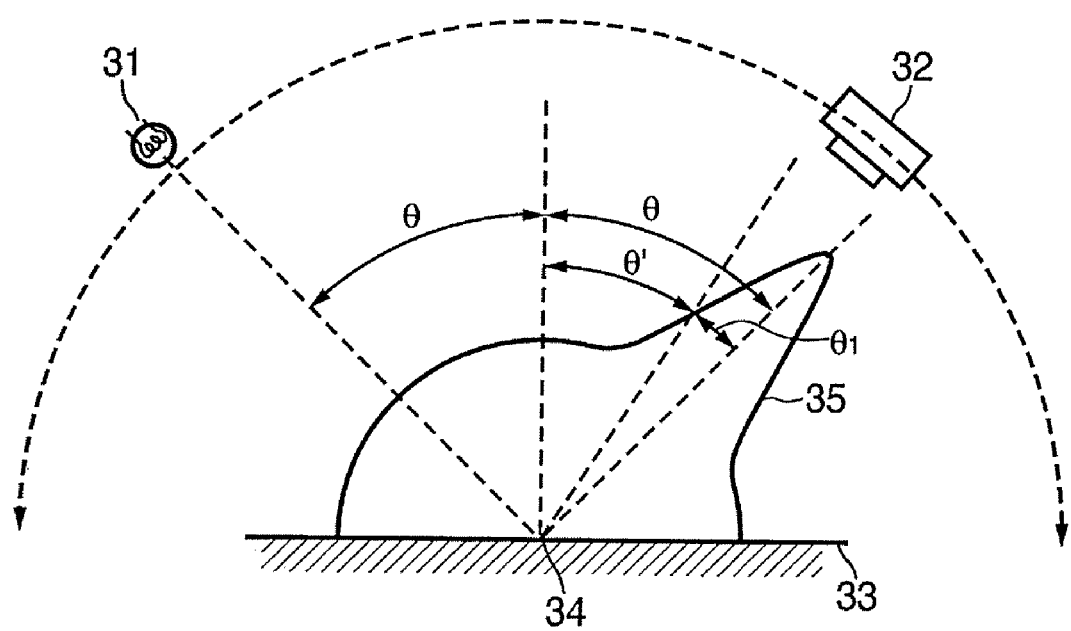
FIG. 3 is a view showing an overview of the overall arrangement and operation of a measurement apparatus which implements a spatial distributed characteristic of reflection measurement unit.

FIG. 3 is a view showing an overview of the overall arrangement and operation of the measurement apparatus which implements the spatial distributed characteristic of reflection measurement unit.

The photometry method of the spatial distributed characteristic of reflection in step S101 will be described below using FIG. 3. When a light source 31 irradiates a to-be-measured part 34 of a printing medium surface 33 to be evaluated with light, a reflection distribution 35 of a different shape is generated due to the irregularity of the printing medium surface 33, the refractive index of a surface material, and the like. A light-receiving device 32 measures the spatial intensity character of this reflection distribution 35 at a plurality of angles on an identical circumference having the to-be-measured part 34 as the center. In other words, the light-receiving device 32 performs goniometric measurement of the spatial distribution of reflected light by the to-be-measured part 34 from an identical circumference.

In this way, the measurement apparatus controls the light-receiving device 32 to illuminate the printing medium 33 with light from a direction having a tilt of an arbitrary angle θ with respect to the normal direction to the printing medium 33 and to acquire the intensity character of the spatial reflected light distribution of the printing medium 33. More specifically, the light-receiving device 32 receives reflected light from the printing medium 33 in each of a plurality of a predetermined directions which have a tilt of an angle θ' with respect to the normal direction to the printing medium 33.

Note that the light source 31 comprises, e.g., a halogen lamp. However, the present invention is not limited to such specific light source, and the types of light sources are not particularly limited. For example, the light source 31 may comprise other light sources such as a pulse xenon lamp and the like. The light-receiving device 32 comprises a detector (optical device) such as a photodiode or the like for detecting light, and such device is available as, e.g., a radiance meter or the like. However, the present invention is not limited to this, and the types of light-receiving devices are not particularly limited. For example, other optical sensors (optical devices) may be used as long as they can detect a light intensity.

The evaluate parameter extraction processing in step S102, i.e., some examples of the extraction method of the specular reflected light intensity and specular reflected light neighboring intensity by the specular reflected light intensity extraction unit 214 and specular reflection neighboring light intensity 215 will be described below using FIGS. 2 to 6.

Figure 4:
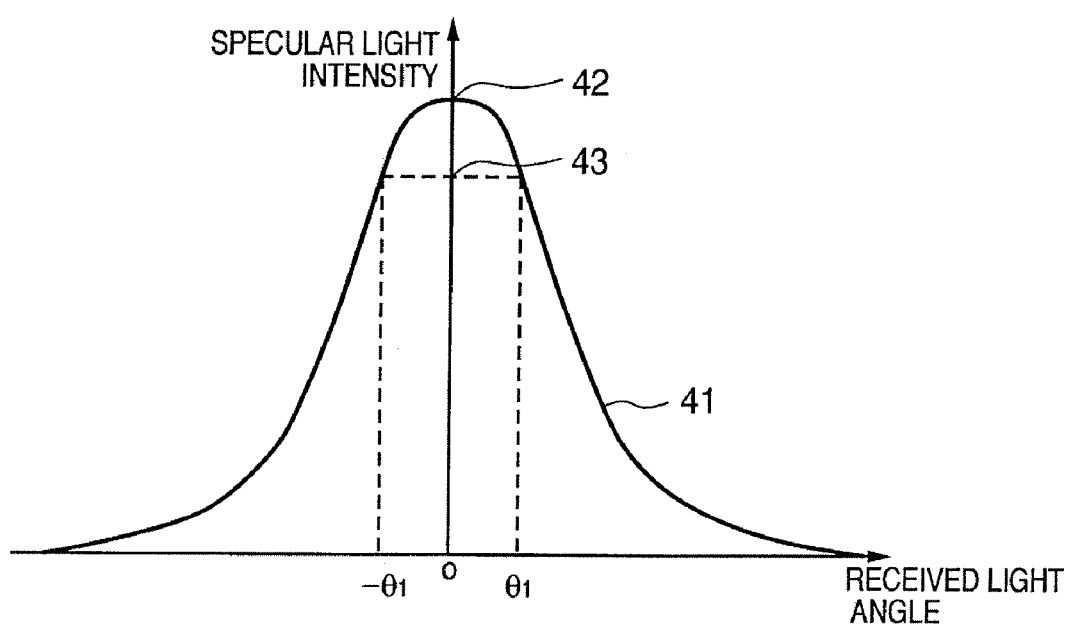
FIG. 4 is a view for explaining an example of an extraction method of a specular reflected light intensity and specular reflected light neighboring intensity according to the first embodiment of the present invention.

FIG. 4 is a view for explaining an example of the extraction method of the specular reflected light intensity and specular reflected light neighboring intensity according to the first embodiment of the present invention.

FIG. 4 shows the reflected light distribution of reflected light intensities at a plurality of received light angles, which are measured by the spatial distributed characteristic of reflection measurement unit 212 in FIG. 3, with the abscissa plotting the received light angle, and the ordinate plotting the received reflected light intensity. Note that the direction of specular reflection with respect to the light source 31 in FIG. 3 is an origin O.

Referring to FIG. 4, a spatial distributed characteristic of reflection 41 corresponds to the reflected light distribution (reflected light intensity distribution character) 35 of the printing medium 33 as an object to be evaluated. A specular reflected light intensity 42 is a light intensity of light received at the origin O, i.e., in the specular reflection direction with respect to the light source 31 (FIG. 3). That is, the specular reflected light intensity to be extracted by the specular reflected light extraction unit 214 in FIG. 2A corresponds to the intensity 42 in FIG. 4. Note that the specular reflected light intensity to be extracted by the specular reflected light extraction unit 214 may be determined by acquiring a maximum value from the spatial distributed characteristic of reflection 41.

By contrast, the specular reflection neighboring light intensity corresponds to a light intensity 43 in FIG. 4. This intensity is a reflected light intensity at an angle $\theta_1$ that deviates from the origin O, the specular reflection direction with respect to the light source 31 by a predetermined angle. The specular reflection neighboring light intensity to be extracted by the specular reflection neighboring light intensity extraction unit 215 in FIG. 2A corresponds to the intensity 43 in FIG. 4. Note that the specular reflection neighboring light intensity to be extracted by the specular reflection neighboring light intensity extraction unit 215 may be determined by acquiring the sum or average value of the reflected light intensity at the angle $\theta_1$ which deviates from the origin O by a predetermined angle, and that at an angle which deviates from the origin in the opposite direction by the same angle $\theta_1$.

Another example of the extraction method of the specular reflected light intensity and specular reflected light neighboring intensity will be described below using FIG. 5.

Figure 5:
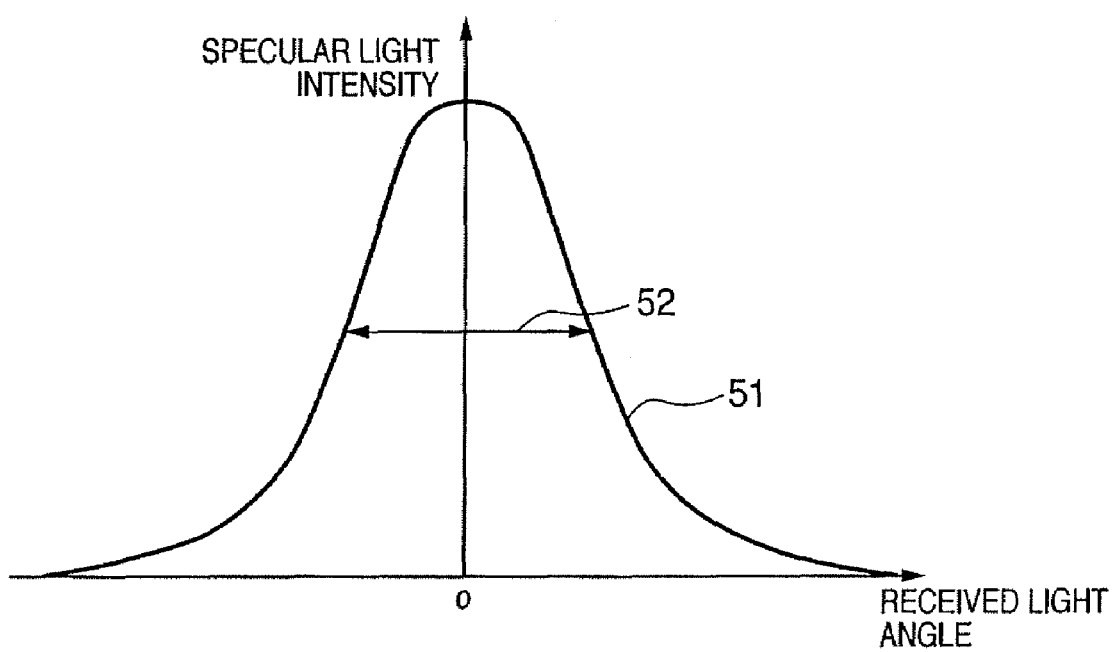
FIG. 5 is a view for explaining another example of an extraction method of a specular reflected light intensity and specular reflected light neighboring intensity according to the first embodiment of the present invention.

FIG. 5 is a view for explaining another example of the extraction method of the specular reflected light intensity and specular reflected light neighboring intensity according to the first embodiment of the present invention.

FIG. 5 shows the reflected light distribution of reflected light intensities at a plurality of received light angles, which are measured by the spatial distributed characteristic of reflection measurement unit 212 in FIG. 3, with the abscissa plotting the received light angle, and the ordinate plotting the received reflected light intensity, as in FIG. 4.

A width index value 52 is the width of the received light angle, which yields a half value of a maximum value of a spatial distributed characteristic of reflection 51, i.e., a full width at half maximum. FIG. 5 exemplifies a case in which the specular reflection neighboring light intensity to be extracted by specular reflection neighboring light intensity extraction unit 215 uses the width index value 52. Note that the width index value 52 may use a width at an arbitrary height (a spread of the reflected light distribution in the neighborhood of specular reflection) such as a width corresponding to 1/10 of the maximum value, that corresponding to 1/100 of the maximum value, and so forth. Furthermore, the aforementioned width corresponding to the half of the full width such as the full width at half maximum or the like may be set as the width index value 52.

Still another example of the extraction method of the specular reflected light intensity and specular reflected light neighboring intensity will be described below using FIG. 6.

Figure 6:
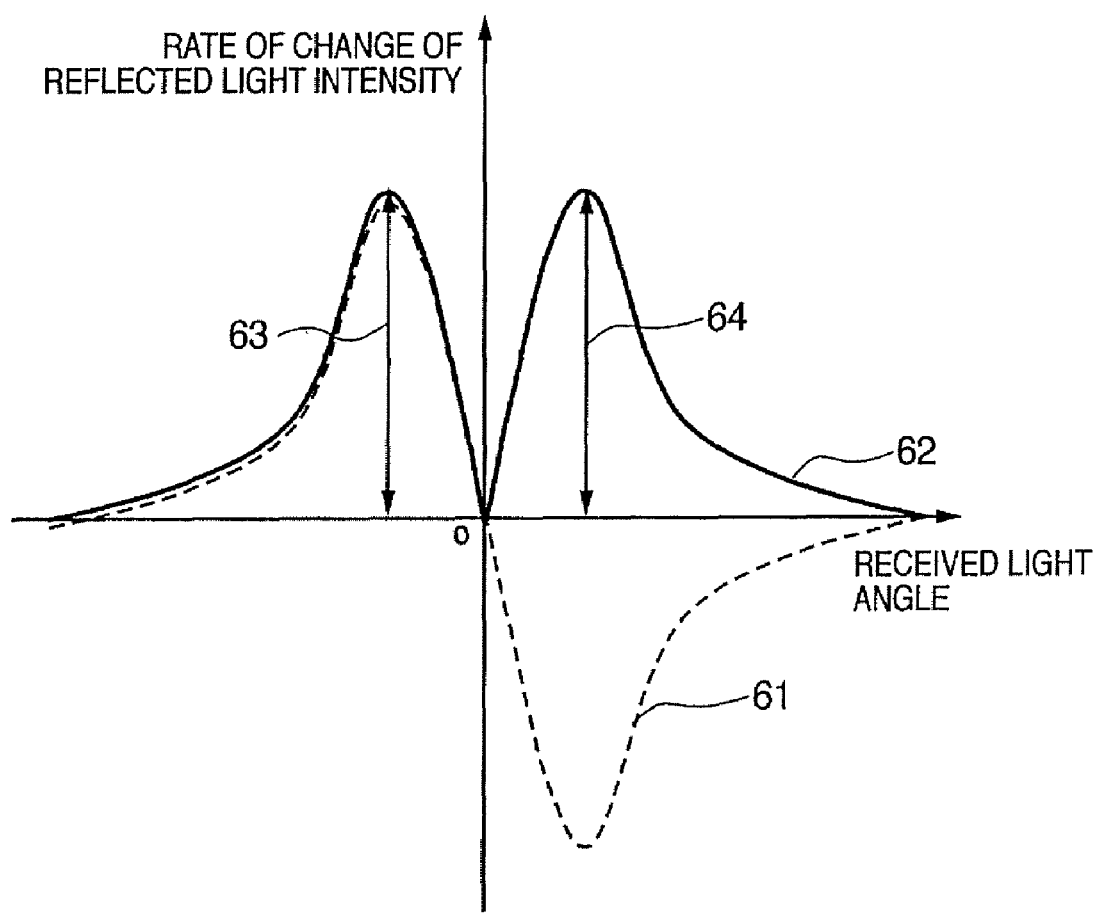
FIG. 6 is a view for explaining still another example of an extraction method of a specular reflected light intensity and specular reflected light neighboring intensity according to the first embodiment of the present invention.

FIG. 6 is a view for explaining still another example of the extraction method of the specular reflected light intensity and specular reflected light neighboring intensity according to the first embodiment of the present invention.

Primary derivative values 61 of the reflected light intensities indicated by the broken curve in FIG. 6 are those for angles of reflected light intensities at the plurality of received light angles in FIG. 4. FIG. 6 exemplifies an example in which the specular reflection neighboring light intensity to be extracted by the specular reflection neighboring light intensity extraction unit 215 uses a standard deviation (a value corresponding to the spread of the reflected light distribution in the neighborhood of specular reflection) of the primary derivative values 61 of the reflected light intensities within a predetermined angle range.

On the other hand, the solid curve shown in FIG. 6 shows the absolute values of the primary derivative values for the angles of the reflected light intensities at the plurality of received light angles in FIG. 4. A maximum rate of increasing 63 and maximum rate of decreasing 64 respectively indicate positions where the rate of change with respect to the angle of the reflected light intensity is largest. The specular reflection neighboring light intensity to be extracted by the specular reflection neighboring light intensity extraction unit 215 may use the maximum rate of increasing 63 and maximum rate of decreasing 64. Alternatively, it may use the sum or average value of the maximum rate of increasing 63 and maximum rate of decreasing 64.

Upon extracting the specular reflection neighboring light intensity based on the primary derivative values for the angles of the reflected light intensities at the plurality of received light angles, a predetermined low-pass filter may be applied to primary derivative to reduce noise upon measurement.

In order to extract the specular reflected light intensity or specular reflection neighboring light intensity from thespatial distributed characteristic of reflection, predetermined interpolation processing or fitting processing may be applied to measured data at the plurality of received light angles.

As the extraction method of the specular reflected light intensity and specular reflection neighboring light intensity, the specular glossiness measurement method (JIS Z 8741), reflection haze measurement method (ISO 13803, ASTM E 430), image clarity measurement method (JIS K 7105, JIS H 8686), and the like may be used in addition to the method using thespatial distributed characteristic of reflection.

As an example using these methods, when the specular glossiness measurement method and reflection haze measurement method are used, the evaluate parameter is a value calculated from a predetermined conversion formula using a specular glossiness value measured based on the specular glossiness measurement method and a reflection haze value measured based on the reflection haze measurement method.

When the specular glossiness measurement method and image clarity measurement method are used, the evaluate parameter is a value calculated by a predetermined conversion formula using a specular glossiness value measured based on the specular glossiness measurement method and an image clarity value measured based on the image clarity measurement method.

The specular reflected light intensity is preferably an index value indicating the brightness of appearance of illumination on the object surface, and the specular reflection neighboring light intensity is preferably an index value indicating the clarity of appearance of illumination on the object surface. The specular reflected light intensity and specular reflection neighboring light intensity preferably undergo predetermined scale calibration in correspondence with the human sensitivity before they are input to the evaluate parameter input unit 221.

The descriptions of FIGS. 4 to 6 have been made taking simple extraction of the reflected light intensity as an evaluate parameter as an example. However, index values (optical character values) based on the intensity of reflected light such as a reflectance, luminance, lightness, and the like may be extracted as evaluate parameters.

The evaluate parameter input processing in step S103 and the evaluate parameter storage processing in step S104 will be described below using FIGS. 2A and 2B, and FIGS. 7 and 8.

Figure 7:
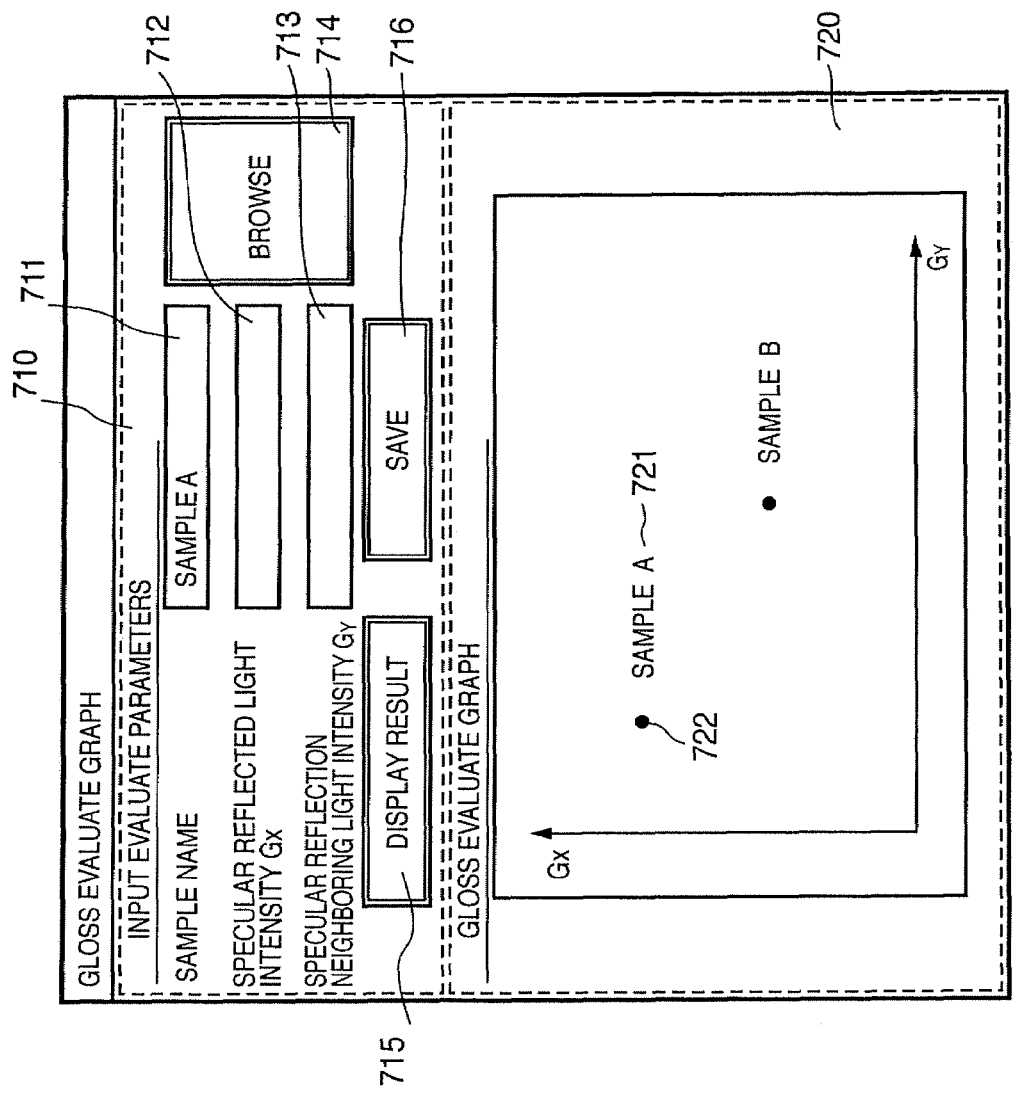
FIG. 7 shows an example of a GUI (graphic user interface) that implements evaluate value input/storage/display processing according to the first embodiment of the present invention.
Figure 8:
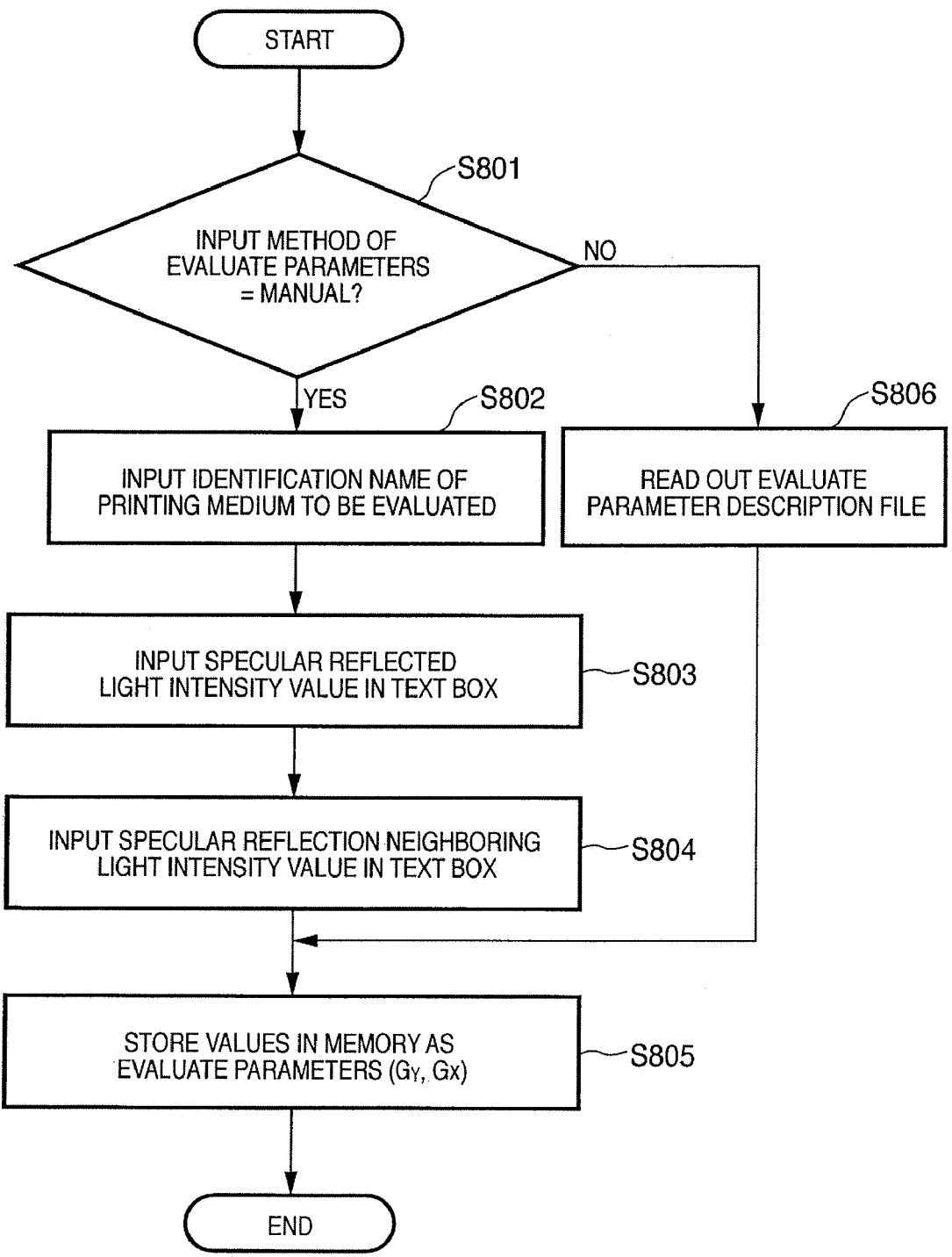
FIG. 8 is a flowchart showing evaluate parameter input processing and storage processing according to the first embodiment of the present invention.

FIG. 7 shows an example of a GUI (graphic user interface) used to implement the evaluate value input/storage/display processing according to the first embodiment of the present invention. FIG. 8 is a flowchart showing the evaluate parameter input processing and storage processing according to the first embodiment of the present invention.

An evaluate parameter input area 710 implements the processing of the evaluate parameter input unit 221 and evaluate parameter storage unit 224 shown in FIG. 2A. Pressing of an evaluate result file output button 716 implements the processing of the gloss evaluate value file output unit 231. Pressing of an evaluate result display button 715 implements the processing of the gloss evaluate value monitor display unit 232.

The evaluate parameters are input manually or automatically by pressing an evaluate parameter browse button 714 to read out an evaluate parameter description file to which evaluate parameters (the specular reflected light intensity and specular reflection neighboring light intensity values stored in a predetermined format) are input in advance.

It is checked first if the evaluate parameter input method is a manual method (step S801). If the evaluate parameters are input manually (YES in step S801), the user inputs an identification name of the printing medium to be evaluated in an evaluate sample name input field 711 (step S802).

Next, the user inputs the specular reflected light intensity value (step S803) This processing is implemented as that of the specular reflected light intensity input unit 222 when the user inputs the specular reflected light intensity value extracted by the specular reflected light intensity extraction unit 214 in a text box of specular reflected light intensity input field 712.

The user then inputs the specular reflection neighboring light intensity value (step S803). This processing is implemented as that of the specular reflection neighboring light intensity input unit 223 when the user inputs the specular reflection neighboring light intensity value extracted by the specular reflected light neighboring intensity extraction unit 215 in a text box of a specular reflected light intensity input field 713.

The identification name of the printing medium to be evaluated and the specular reflected light intensity and specular reflection neighboring light intensity values (evaluate parameters ($G_x$, $G_y$)) input in steps S802 to S804 are stored in the main memory 102 (step S805).

On the other hand, if the user presses the evaluate parameter browse button 714 (NO in step S801), the designated evaluate parameter description file is read out from the storage medium such as the HDD 105 or the like (step S806). The identification name of the printing medium to be evaluated and the specular reflected light intensity and specular reflection neighboring light intensity values (evaluate parameters ($G_x$, $G_y$)) described in this file are stored in the main memory 102 (step S805).

Note that operations for various controls (buttons, text boxes, and the like) which form the graphic user interface shown in FIG. 7 are executed using the input devices such as the keyboard 111, mouse 112, and the like. The user operates various controls prepared on the user interface using these input devices, thus implementing desired operations.

The evaluate parameter display processing in step S105 will be described below using FIGS. 7 and 9.

Figure 9:
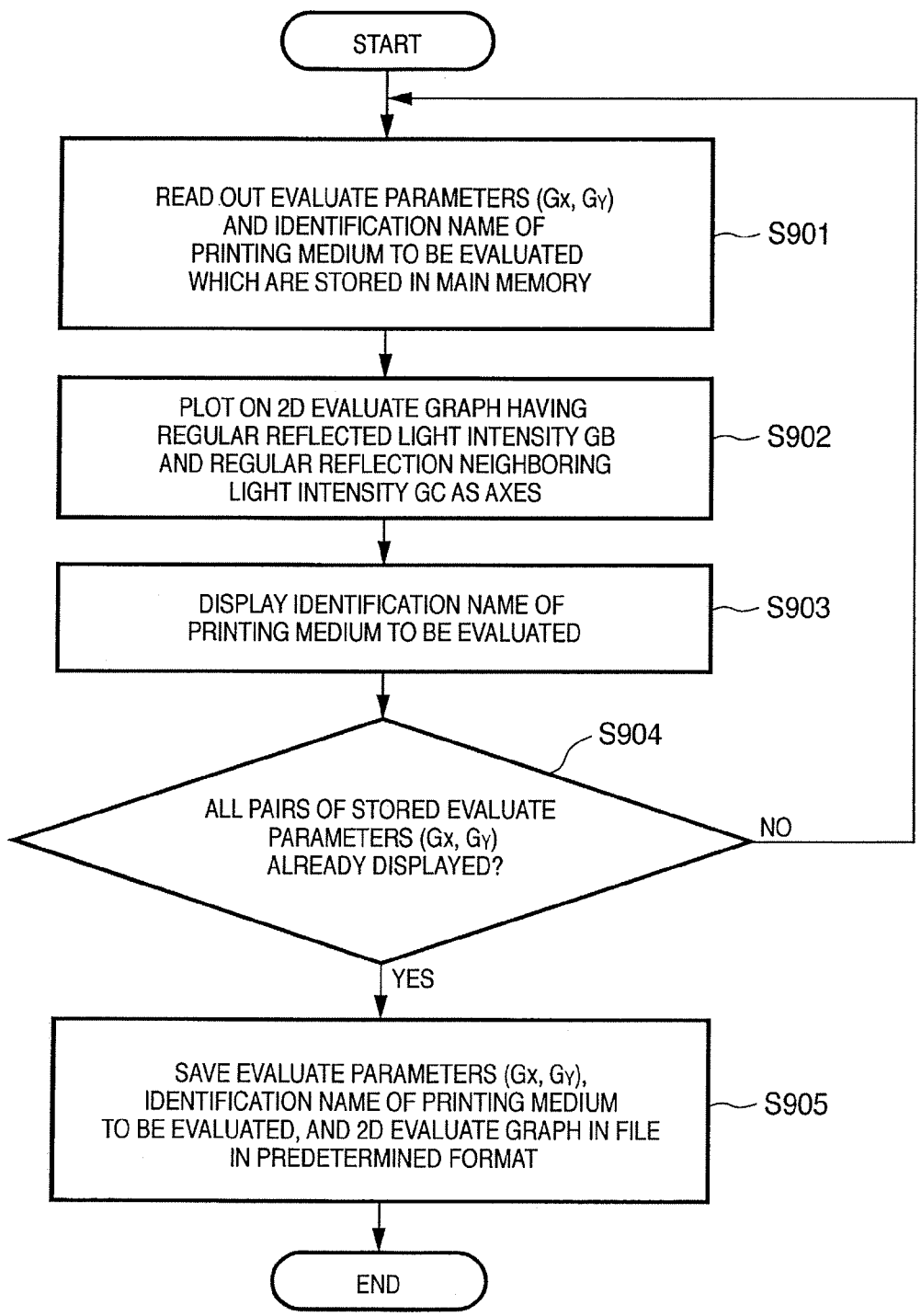
FIG. 9 is a flowchart showing evaluate parameter display processing according to the first embodiment of the present invention.

FIG. 9 is a flowchart showing the evaluate parameter display processing according to the first embodiment of the present invention.

Note that FIG. 9 shows the processing in the gloss evaluate value monitor display unit 232 which displays the gloss evaluate value based on the evaluate parameters of the printing medium to be evaluated, which are stored by the evaluate parameter storage unit 224, and in the gloss evaluate value file output unit 231 which outputs the gloss evaluate value to a file in a predetermined format.

The processing of FIG. 9 starts in response to pressing of the evaluate result display button 715 on the GUI in FIG. 7.

The pair of the specular reflected light intensity and specular reflection neighboring light intensity values stored in the main memory 102 as the evaluate parameters ($G_x$, $G_y$) and the identification name of the corresponding printing medium to be evaluated are read out (step S901). The readout parameters ($G_x$, $G_y$) are plotted on a 2D evaluate graph which has a specular reflected light intensity $G_y$ and specular reflection neighboring light intensity $G_x$ as axes on a gloss evaluate value display area 720 as a gloss evaluate value 722 (step S902).

The identification name of the corresponding printing medium to be evaluated read out in step S901 is displayed as a sample name label 721 near a point indicating the gloss evaluate value 722 plotted on the gloss evaluate value display area 720 (step S903).

The abscissa of the 2D evaluate graph shown in FIG. 7 demonstrates that an image of illumination and that of another object which appear on the object surface become clearer as the value approaches zero. The ordinate demonstrates that the image of illumination which appears on the object surface becomes brighter as the value increases.

Therefore, the example shown in FIG. 7 represents that the image of illumination and that of another object of sample A are clearer and brighter than those of sample B. For this reason, as can be seen from FIG. 7, the gloss of sample A is higher than that of sample B.

If the evaluate parameter input method selected in step S801 is an automatic method, the evaluate parameter description file storage unit 224 may store a plurality of pairs of evaluate parameters ($G_x$, $G_y$) In such case, it is checked if all the pairs of evaluate parameters ($G_x$, $G_y$) stored in the evaluate parameter description file storage unit 224 are displayed, and the processes in steps S901 to S903 are repeated until all the pairs of evaluate parameters ($G_x$, $G_y$) are displayed (step S904).

The gloss evaluate value $G_v$ as the gloss character of the printing medium to be evaluated is calculated as a linear sum obtained by multiplying the evaluate parameters stored in the evaluate parameter description file storage unit 224 by predetermined weighting coefficients by:

$$G_V = \alpha G_Y + \beta G_X + \gamma \quad (1)$$

$\begin{cases} G_V: \text{glossiness evaluation value} \\ G_Y: \text{regular reflected light intensity} \\ G_X: \text{regular reflection neighboring reflected light intensity} \\ \alpha, \beta: \text{weighting coefficients} \\ \gamma: \text{constant} \end{cases}$ Finally, upon pressing of the evaluate result file output button 716, the evaluate parameters ($G_x$, $G_y$), the identification name of the printing medium to be evaluated, and the 2D evaluate graph are output to a file in a predetermined format, and the output file is stored in an external storage medium such as the HDD 105 or the like (step S905).

As described above, according to the first embodiment, since the specular reflected light intensity and specular reflection neighboring light intensity values as the evaluate parameters, which serve as evaluate indices of the gloss of an object are expressed and presented on at least a two-dimensional space specified by these evaluate parameters, the gloss level of the object can be quantitatively evaluated to have high correlation with one's subjective gloss compared to the conventional method.

Second Embodiment

The second embodiment of the present invention will be described hereinafter. The arrangement of a gloss and gloss nonuniformity evaluate value apparatus includes the same received light signal processor as the received light signal processor 210 in FIG. 2A of the first embodiment. Therefore, the second embodiment will especially explain only a calculation unit and output unit of an evaluate value as differences from the first embodiment.

Figure 10:
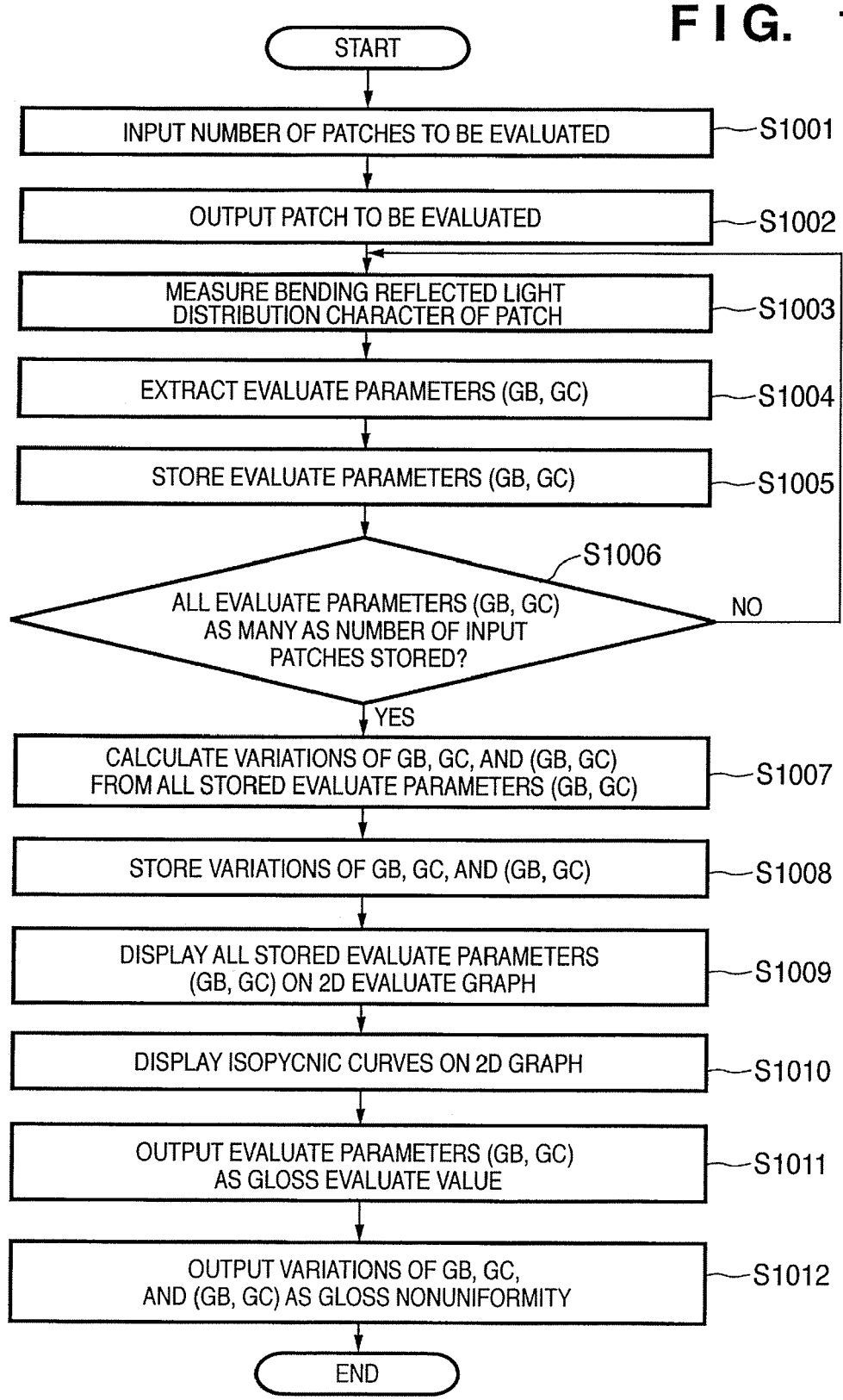
FIG. 10 is a flowchart showing display/output processing of evaluate values of gloss and gloss nonuniformity of printing media to be evaluated according to the second embodiment.

FIG. 10 is a flowchart showing the display/output processing of gloss and gloss nonuniformity evaluate values of a printing medium to be evaluated according to the second embodiment.

The number of patches to be evaluated is input (step S1001). An arbitrary patch to be evaluated is output using a desired image output apparatus (e.g., the printer 116) (step S1002). The spatial distributed characteristic of reflection of each output patch is measured (step S1003). Evaluate parameters ($G_x$, $G_y$) of each patch are extracted from the measured spatial distributed characteristic of reflection (step S1004). The extracted evaluate parameters ($G_x$, $G_y$) are stored in the main memory 102 (step S1005).

It is then checked if the number of pairs of evaluate parameters ($G_x$, $G_y$) stored in the main memory 102 reaches the number of input patches. In other words, it is checked if the pairs of evaluate parameters ($G_x$, $G_y$) as many as the number of input patches are stored in the main memory 102 (step S1006).

If not all the pairs of evaluate parameters ($G_x$, $G_y$) are stored in the main memory 102 (NO in step S1006), the processes in steps S1003 to S1005 are repeated until all the pairs of evaluate parameters ($G_x$, $G_y$) are stored in the main memory 102.

If all the pairs of evaluate parameters ($G_x$, $G_y$) are stored in the main memory 102 (YES in step S1006), variations of $G_x$, those of $G_y$, and those of ($G_x$, $G_y$) are calculated from all the pairs of evaluate parameters ($G_x$, $G_y$) stored in the main memory 102 (step S1007).

The calculated variations of $G_x$, those of $G_y$, and those of ($G_x$, $G_y$) are stored in the main memory 102 (step S1008) Next, all the evaluate parameters ($G_x$, $G_y$) are plotted on a 2D evaluate graph as in the first embodiment, and plotted points are set as gloss evaluate values of the respective patches (step S1009).

Isopycnic curves are calculated from the plotted points, and are displayed on the 2D evaluate graph (step S1010). Finally, the evaluate parameters ($G_x$, $G_y$) and the variations of $G_x$, $G_y$, and ($G_x$, $G_y$) are respectively output as gloss evaluate values and gloss nonuniformity values to a file in a predetermined format (step S1012).

The contents of the processes in respective steps will be described in detail below with reference to FIG. 11.

Figure 11:
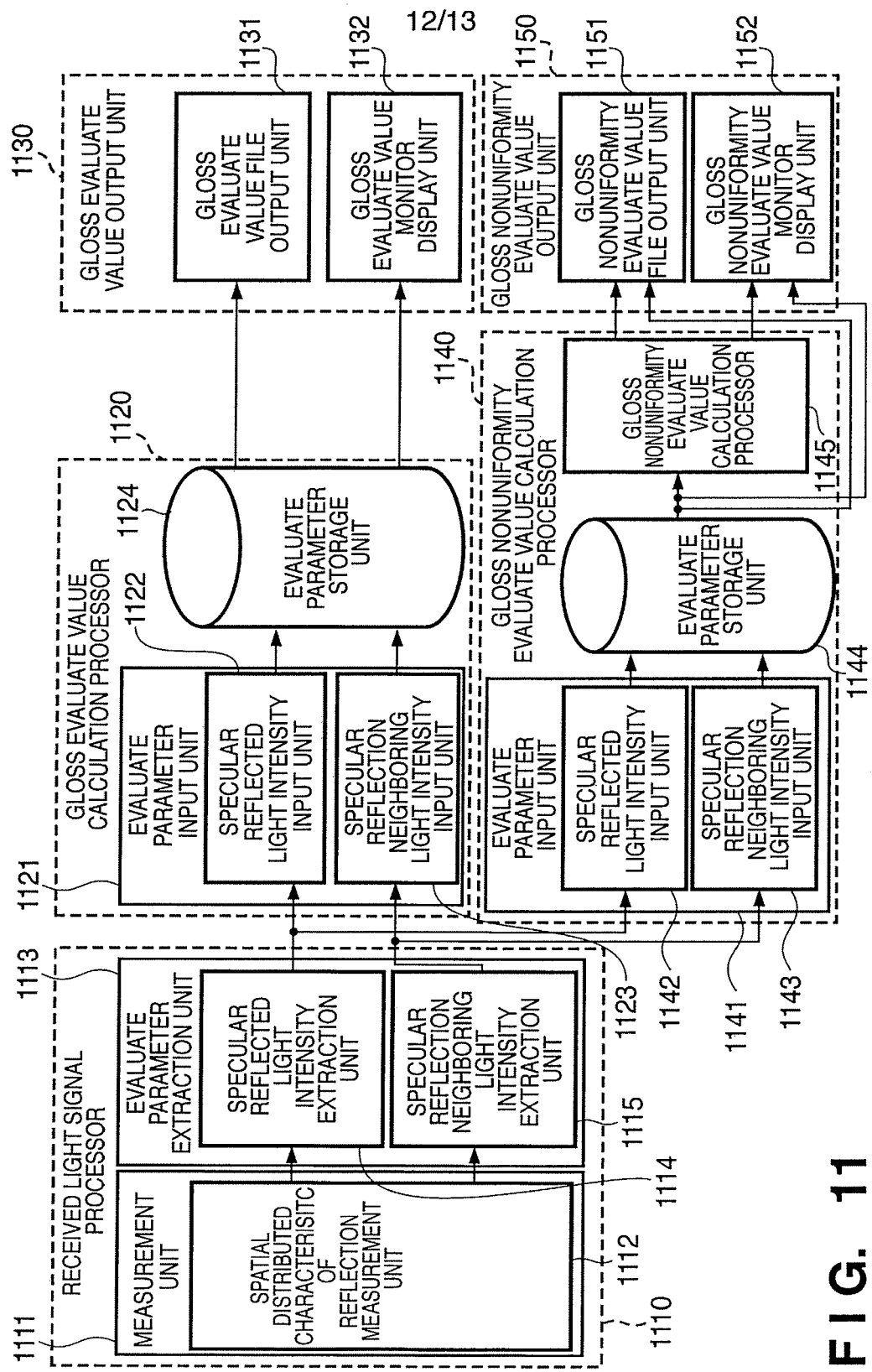
FIG. 11 is a schematic block diagram showing the overall arrangement of a gloss and gloss nonuniformity evaluating apparatus according to the second embodiment of the present invention.

FIG. 11 is a schematic block diagram showing the overall arrangement of a gloss and gloss nonuniformity evaluating apparatus according to the second embodiment of the present invention.

As described above, the received light signal processor 210 in FIG. 2A of the first embodiment and a received light signal processor 1110 in FIG. 11 are implemented by the same arrangement. Also, since a gloss evaluate value calculation processor 1120 and gloss evaluate value output unit 1130 are implemented by substantially the same arrangement, only a gloss nonuniformity evaluate value calculation processor 1140 and gloss nonuniformity evaluate value output unit 1150 as the differences from the first embodiment will be described in detail below.

The gloss nonuniformity evaluate value calculation processor 1140 includes an evaluate parameter input unit 1141, evaluate parameter storage unit 1144, and gloss nonuniformity evaluate value arithmetic unit 1145. The evaluate parameter input unit 1141 includes a specular reflected light intensity input unit 1142 and specular reflection neighboring light intensity 1143 which respectively input specular reflected light intensities and specular reflection neighboring light intensities for two or more different types of patches extracted by an evaluate parameter extraction unit 1113.

The evaluate parameter storage unit stores the specular reflected light intensities and specular reflection neighboring light intensities input by the evaluate parameter input unit 1141 as pairs. After the evaluate parameter storage unit 1144 stores the pairs of specular reflected light intensities and specular reflection neighboring light intensities as many as the number of patches input in step S1001, the gloss nonuniformity evaluate value arithmetic unit 1145 executes predetermined arithmetic processing in step S1007.

This predetermined arithmetic processing is based on the following equations (2) which calculates nonuniformity components $\sigma(G_y)$ of the specular reflected light intensities, nonuniformity components $\sigma(G_x)$ of the specular reflection neighboring light intensities, and gloss nonuniformity evaluate values $\sigma(G_x, G_y)$ for a plurality of patches:

$$\sigma(G_Y) = \sqrt{\frac{n \sum G_Y^2 - (\sum G_Y)^2}{n(n-1)}} \quad (2)$$

$$\sigma(G_X) = \sqrt{\frac{n \sum G_X^2 - (\sum G_X)^2}{n(n-1)}}$$

$$\sigma(G_X, G_X) = \sqrt{\frac{n \sum G_Y^2 - (\sum G_Y)^2}{n(n-1)}} \cdot \sqrt{\frac{n \sum G_X^2 - (\sum G_X)^2}{n(n-1)}}$$

$G_Y$: regular reflected light intensity
$G_X$: regular reflection neighboring reflected light intensity
$\sigma(G_Y)$: nonuniformity component in regular reflected light intensity
$\sigma(G_X)$: nonuniformity component in regular reflection neighboring light intensity
$\sigma(G_Y, G_X)$: gloss nonuniformity evaluate value
$n$: number of patches to be evaluated As will be described later, the isopycnic curves may be calculated from the gloss evaluate values of respective patches, and the gloss nonuniformity evaluate values $\sigma(G_x, G_y)$ may be calculated from the gradients of the isopycnic curves.

The gloss nonuniformity evaluate value output unit 1150 includes a gloss nonuniformity evaluate value file output unit 1151 and gloss nonuniformity evaluate value monitor display unit 1152. The gloss nonuniformity evaluate value file output unit 1151 outputs the gloss nonuniformity evaluate values σ($G_x$, $G_y$), nonuniformity components σ($G_y$) of the specular reflected light intensities, and nonuniformity components σ($G_x$) of the specular reflection neighboring light intensities, which are calculated by equations (2) above to a file in a predetermined format.

An example of a GUI used to implement the display processing by the gloss nonuniformity evaluate value monitor display unit 1152 will be described below using FIG. 12.

Figure 12:
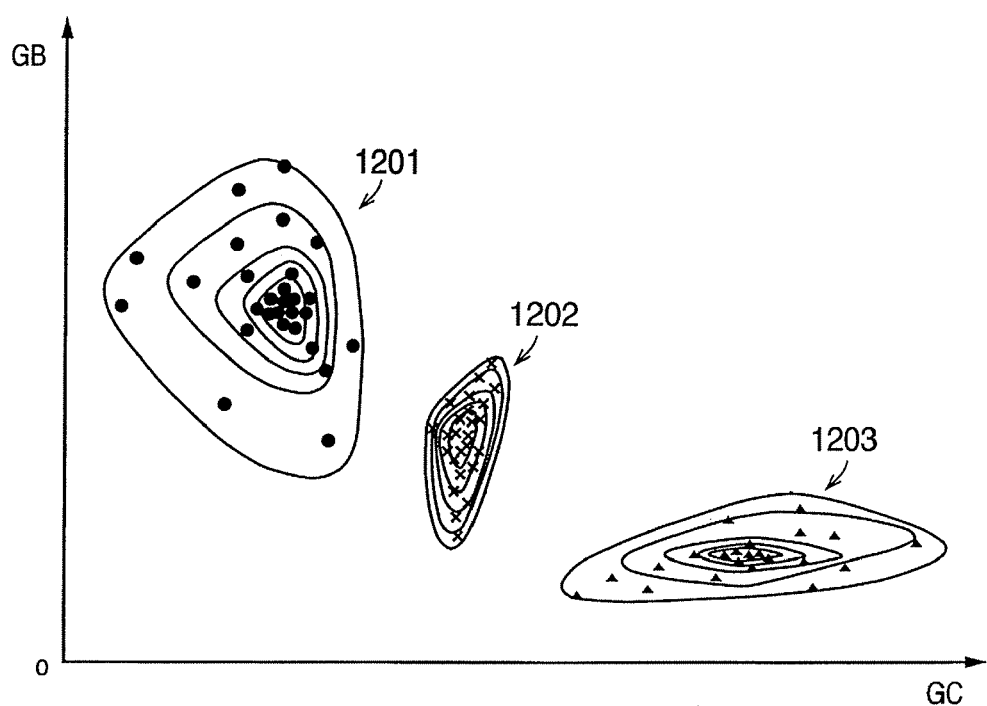
FIG. 12 shows an example of a GUI that implements display processing according to the second embodiment of the present invention.

FIG. 12 shows an example of the GUI used to implement the display processing according to the second embodiment of the present invention.

FIG. 12 shows the GUI which allows the user to visually recognize the gloss nonuniformity.

In FIG. 12 ($G_x$, $G_y$) are plotted as gloss evaluate values of respective patches on the 2D evaluate graph on the color monitor 107, and isopycnic curves are calculated from plotted points and are displayed on the 2D evaluate graph.

Reference numeral 1201 denotes isopycnic curves which represent the state of gloss nonuniformity of given sample group A, and ● indicates the gloss evaluate values of respective patches of sample group B.

Reference numeral 1202 denotes gloss nonuniformity of sample group B, and x represents the gloss evaluate values of respective patches of sample group B.

Reference numeral 1203 denotes gloss nonuniformity of sample group C, and ▲ represents the gloss evaluate values of respective patches of sample group C.

As can be read from FIG. 12, since the gloss evaluate values ($G_x$, $G_y$) of sample group A distribute broader than sample group B, the gloss nonuniformity of sample group A is larger than that of sample group B. Also, as can be seen from FIG. 12, sample group B distribute relatively in the direction of the ordinate; it has larger nonuniformity of the specular reflected light intensities. On the other hand, as can be seen from FIG. 12, sample group C distributes relatively in the direction of the abscissa; it has larger nonuniformity of specular reflection neighboring light intensities.

As described above, according to the second embodiment, the user can visually recognize the gloss nonuniformity based on the intervals of the isopycnic curves, in addition to the effects described in the first embodiment.

In the first and second embodiments, information used to evaluate the optical character of an object is presented on the 2D space specified by the evaluate parameters. However, three evaluate parameters may be used, and information used to evaluate the optical character of an object may be presented on a three-dimensional space specified by these parameters. For example, a three-dimensional configuration may be adopted by adding, e.g., orange peel components.

The preferred embodiments have been explained, and the present invention can be practiced in the forms of a system, apparatus, method, program, storage medium, and the like. More specifically, the present invention can be applied to either a system constituted by a plurality of devices, or an apparatus consisting of a single equipment.

Note that the present invention includes a case wherein the invention is achieved by directly or remotely supplying a program of software that implements the functions of the aforementioned embodiments (programs corresponding to the illustrated flow charts in the above embodiments) to a system or apparatus, and reading out and executing the supplied program code by a computer of that system or apparatus.

Therefore, the program code itself installed in a computer to implement the functional processing of the present invention using the computer implements the present invention. That is, the present invention includes the computer program itself for implementing the functional processing of the present invention.

In this case, the form of program is not particularly limited, and an object code, a program to be executed by an interpreter, script data to be supplied to an OS, and the like may be used as along as they have the program function.

As a recording medium for supplying the program, for example, a floppy (tradename) disk, hard disk, optical disk, magneto-optical disk, MO, CD-ROM, CD-R, CD-RW, magnetic tape, nonvolatile memory card, ROM, DVD (DVD-ROM, DVD-R), and the like may be used.

As another program supply method, the program may be supplied by establishing connection to a home page on the Internet using a browser on a client computer, and downloading the computer program itself of the present invention or a compressed file containing an automatic installation function from the home page onto a recording medium such as a hard disk or the like. Also, the program code that forms the program of the present invention may be segmented into a plurality of files, which may be downloaded from different home pages. That is, the present invention includes a WWW server which makes a plurality of users download a program file required to implement the functional processing of the present invention by the computer.

Also, a storage medium such as a CD-ROM or the like, which stores the encrypted program of the present invention, may be delivered to the user, the user who has cleared a predetermined condition may be allowed to download key information that decrypts the program from a home page via the Internet, and the encrypted program may be executed using that key information to be installed on a computer, thus implementing the present invention.

The functions of the aforementioned embodiments may be implemented not only by executing the readout program code by the computer but also by some or all of actual processing operations executed by an OS or the like running on the computer on the basis of an instruction of that program.

Furthermore, the functions of the aforementioned embodiments may be implemented by some or all of actual processes executed by a CPU or the like arranged in a function extension board or a function extension unit, which is inserted in or connected to the computer, after the program read out from the recording medium is written in a memory of the extension board or unit.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2005-082709, filed Mar. 22, 2005, which is hereby incorporated by reference herein in its entirety.

The invention claimed is:

1. An information processing apparatus for evaluating a gloss character of an object, comprising:
   an acquisition unit adapted to acquire a measured value obtained by measuring the object using a measurement device that measures a light intensity from the object illuminated with light;

a calculation unit adapted to calculate a specular reflected light intensity and a specular reflection neighboring light intensity from the measured value; and a display unit adapted to visually display the specular reflected light intensity and the specular reflection neighboring light intensity calculated by said calculation unit on a space of at least two dimensions, wherein said acquisition unit acquires a spatial distributed characteristic of reflection of the object, and the specular reflection neighboring light intensity is a width between two points on a graph, which is defined by an abscissa axis of the spatial distributed characteristic of reflection and an ordinate axis of a reflected light intensity, intersected by a hypothetical line extended horizontally from a reflected light intensity on the ordinate axis.

2. The apparatus according to claim 1, wherein the specular reflected light intensity is an index value indicating brightness of appearance of illumination on an object surface, and the specular reflection neighboring light intensity is an index value indicating clarity of appearance of illumination on the object surface.

3. The apparatus according to claim 1, further comprising a gloss evaluate value calculation unit adapted to calculate a gloss evaluate value from the specular reflected light intensity and the specular reflection neighboring light intensity.

4. The apparatus according to claim 1, wherein said acquisition unit acquires the measured value for each of a plurality of patches, and said apparatus further comprises:

a standard deviation calculation unit adapted to calculate a standard deviation of specular reflected light intensities and a standard deviation of specular reflection neighboring light intensities based on the specular reflected light intensities and the specular reflection neighboring light intensities for the plurality of patches; and a gloss nonuniformity evaluate value calculation unit adapted to calculate a gloss nonuniformity evaluate value from the standard deviation of the specular reflected light intensities and the standard deviation of the specular reflection neighboring light intensities.

5. The apparatus according to claim 1, wherein said display unit visually displays using a three-dimensional space using the specular reflected light intensity, the specular reflection neighboring light intensity, and still orange peel components.

6. An information processing apparatus for evaluating a gloss character of an object, comprising:

an acquisition unit adapted to acquire a measured value obtained by measuring the object using a measurement device that measures a light intensity from the object illuminated with light;

a calculation unit adapted to calculate a specular reflected light intensity and a specular reflection neighboring light intensity from the measured value; and a display unit adapted to visually display the specular reflected light intensity and the specular reflection neighboring light intensity calculated by said calculation unit on a space of at least two dimensions, wherein said acquisition unit acquires a spatial distributed characteristic of reflection of the object, and the specular reflection neighboring light intensity is calculated from a maximum rate of increasing and a minimum rate of decreasing of a primary derivative value of a reflected light intensity at an angle that deviates from a specular reflection direction by a predetermined angle.

7. An information processing apparatus for evaluating a gloss character of an object, comprising:

an acquisition unit adapted to acquire a measured value obtained by measuring the object using a measurement device that measures a light intensity from the object illuminated with light;

a calculation unit adapted to calculate a specular reflected light intensity and a specular reflection neighboring light intensity from the measured value; and a display unit adapted to visually display the specular reflected light intensity and the specular reflection neighboring light intensity calculated by said calculation unit on a space of at least two dimensions, wherein said acquisition unit acquires a specular glossiness value measured based on a specular glossiness measurement method, and a reflection haze value measured based on a reflection haze measurement method.

8. An information processing apparatus for evaluating a gloss character of an object, comprising:

an acquisition unit adapted to acquire a measured value obtained by measuring the object using a measurement device that measures a light intensity from the object illuminated with light;

a calculation unit adapted to calculate a specular reflected light intensity and a specular reflection neighboring light intensity from the measured value; and a display unit adapted to visually display the specular reflected light intensity and the specular reflection neighboring light intensity calculated by said calculation unit on a space of at least two dimensions, wherein said acquisition unit acquires a specular glossiness value measured based on a specular glossiness measurement method, and an image clarity value measured based on an image clarity measurement method.

9. A recording medium storing a program to cause a computer to execute control on an information processing apparatus which evaluates a gloss character of an object, reading and executing the program to cause the computer to execute:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a spatial distributed characteristic of reflection of the object, and the specular reflection neighboring light intensity is a width between two points on a graph, which is defined by an abscissa axis of the spatial distributed characteristic of reflection and an ordinate axis of a reflected light intensity, intersected by a hypothetical line extended horizontally from a reflected light intensity on the ordinate axis.

10. A recording medium storing a program to cause a computer to execute control on an information processing apparatus which evaluates a gloss character of an object, reading and executing the program to cause the computer to execute:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a spatial distributed characteristic of reflection of the object, and the specular reflection neighboring light intensity is calculated from a maximum rate of increasing and a minimum rate of decreasing of a primary derivative value of a reflected light intensity at an angle that deviates from a specular reflection direction by a predetermined angle.

11. A recording medium storing a program to cause a computer to execute control on an information processing apparatus which evaluates a gloss character of an object, reading and executing the program to cause the computer to execute:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a specular glossiness value measured based on a specular glossiness measurement method, and a reflection haze value measured based on a reflection haze measurement method.

12. A recording medium storing a program to cause a computer to execute control on an information processing apparatus which evaluates a gloss character of an object, reading and executing the program to cause the computer to execute:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a specular glossiness value measured based on a specular glossiness measurement method, and an image clarity value measured based on an image clarity measurement method.

13. An information processing method of evaluating a gloss character of an object using an information processing apparatus, comprising:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a spatial distributed characteristic of reflection of the object, and the specular reflection neighboring light intensity is a width between two points on a graph, which is defined by an abscissa axis of the spatial distributed characteristic of reflection and an ordinate axis of a reflected light intensity, intersected by a hypothetical line extended horizontally from a reflected light intensity on the ordinate axis.

14. An information processing method of evaluating a gloss character of an object using an information processing apparatus, comprising:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a spatial distributed characteristic of reflection of the object, and the specular reflection neighboring light intensity is calculated from a maximum rate of increasing and a minimum rate of decreasing of a primary derivative value of a reflected light intensity at an angle that deviates from a specular reflection direction by a predetermined angle.

15. An information processing method of evaluating a gloss character of an object using an information processing apparatus, comprising:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a specular glossiness value measured based on a specular glossiness measurement method, and a reflection haze value measured based on a reflection haze measurement method.

16. An information processing method of evaluating a gloss character of an object using an information processing apparatus, comprising:

an acquisition step of acquiring a measured value obtained by measuring the object using a measurement device that measures a light intensity from the object illuminated with light;

a calculation step of calculating a specular reflected light intensity and a specular reflection neighboring light intensity from the measured value; and a display step of visually displaying the specular reflected light intensity and the specular reflection neighboring light intensity calculated in said calculation step on a space of at least two dimensions, wherein said acquisition step acquires a specular glossiness value measured based on a specular glossiness measurement method, and an image clarity value measured based on an image clarity measurement method.

* * * * *

UNITED STATES PATENT AND TRADEMARK OFFICE
CERTIFICATE OF CORRECTION

| | |
|---|---|
| PATENT NO. | : 7,315,379 B2 |
| APPLICATION NO. | : 11/742065 |
| DATED | : January 1, 2008 |
| INVENTOR(S) | : Takayuki Jinno |

It is certified that error appears in the above-identified patent and that said Letters Patent is hereby corrected as shown below:

IN THE DRAWINGS:
Sheet No. 1, Figure 1, "CHARACTERISITC" should read --CHARACTERISTIC--.
Sheet No. 2, Figure 2A, "CHARACTERISITC" should read --CHARACTERISTIC--.
Sheet No. 12, Figure 11, "CHARACTERISITC" should read --CHARACTERISTIC--.

COLUMN 1:
Line 33, "hase" should read --haze--.

COLUMN 3:
Line 48, "thea" should read --the--.

COLUMN 4:
Line 2, "thea" should read --the--.

COLUMN 6:
Line 16, "such" should read --such as--.

COLUMN 10:
Line 26, "thespa" should read --the spa- --.
Line 36, "thespatial" should read --the spatial--.

COLUMN 11:
Line 31, "(step S803)" should read --(step S803).--.

UNITED STATES PATENT AND TRADEMARK OFFICE
CERTIFICATE OF CORRECTION

PATENT NO. : 7,315,379 B2
APPLICATION NO. : 11/742065
DATED : January 1, 2008
INVENTOR(S) : Takayuki Jinno It is certified that error appears in the above-identified patent and that said Letters Patent is hereby corrected as shown below:

COLUMN 12:
Line 40, "$801" should read --S801--.

Signed and Sealed this

Third Day of February, 2009

JOHN DOLL
*Acting Director of the United States Patent and Trademark Office*